United States Patent
Schmitz et al.

(10) Patent No.: US 9,180,075 B2
(45) Date of Patent: Nov. 10, 2015

(54) CONCENTRATES FOR TREATING SUBSTRATES

(75) Inventors: Jana Schmitz, Hilden (DE); Petra Schulte, Köln (DE); Anja Stork, Köln (DE); Rolf Kawa, Monheim (DE)

(73) Assignee: Cognis IP Management GmbH, Duesseldorf (DE)

( * ) Notice: Subject to any disclaimer, the term of this patent is extended or adjusted under 35 U.S.C. 154(b) by 65 days.

(21) Appl. No.: 13/511,247

(22) PCT Filed: Nov. 16, 2010

(86) PCT No.: PCT/EP2010/006963
§ 371 (c)(1),
(2), (4) Date: May 22, 2012

(87) PCT Pub. No.: WO2011/063902
PCT Pub. Date: Jun. 3, 2011

(65) Prior Publication Data
US 2012/0231059 A1  Sep. 13, 2012

(30) Foreign Application Priority Data
Nov. 25, 2009 (EP) .................................. 09014677

(51) Int. Cl.
| | |
|---|---|
| *A61Q 19/10* | (2006.01) |
| *A61K 8/02* | (2006.01) |
| *B05D 5/00* | (2006.01) |
| *A61Q 19/00* | (2006.01) |
| *A61Q 5/00* | (2006.01) |
| *A61K 8/92* | (2006.01) |
| *A61Q 5/02* | (2006.01) |
| *A61K 8/34* | (2006.01) |
| *A61K 8/37* | (2006.01) |
| *A61K 8/39* | (2006.01) |
| *A61K 8/86* | (2006.01) |

(52) U.S. Cl.
CPC .............. *A61K 8/345* (2013.01); *A61K 8/0208* (2013.01); *A61K 8/375* (2013.01); *A61K 8/39* (2013.01); *A61K 8/86* (2013.01); *A61Q 19/10* (2013.01)

(58) Field of Classification Search
CPC ........... A61K 8/39; A61K 8/86; A61K 8/375; A61K 8/0208; A61K 8/345; A61Q 19/10
See application file for complete search history.

(56) References Cited

U.S. PATENT DOCUMENTS

| | | | | |
|---|---|---|---|---|
| 2005/0008681 | A1* | 1/2005 | Deckner et al. | ................ 424/443 |
| 2005/0009431 | A1* | 1/2005 | Chamba et al. | ................ 442/234 |
| 2007/0292383 | A1 | 12/2007 | Schepky et al. | |

FOREIGN PATENT DOCUMENTS

| | | | |
|---|---|---|---|
| DE | 102005006299 | * | 8/2004 |
| DE | 102005006299 | | 8/2006 |
| EP | 1639989 | | 3/2006 |
| EP | 2090281 | * | 8/2009 |
| JP | H07-138469 | | 5/1995 |
| JP | 2004-203794 | | 7/2004 |
| JP | 2006-117643 | | 5/2006 |
| JP | 2008-266224 | | 11/2008 |
| WO | WO-2005/004835 | | 1/2005 |

OTHER PUBLICATIONS

Issberner et al., DE-102005006299, Machine Translation, Aug. 2004.*
International Search Report in PCT/EP2010/006963, dated May 7, 2012, 3 pgs.
IPRP and Written Opinion in PCT/EP2010/006963, dated Jun. 26, 2012, 8 pgs.
Machine Translation of DE-102005006299, 22 pgs.

* cited by examiner

*Primary Examiner* — Richard Schnizer
*Assistant Examiner* — Katherine Peebles
(74) *Attorney, Agent, or Firm* — Servilla Whitney LLC

(57) ABSTRACT

Described are compositions, containing a. compounds selected from (i.) hydrogenated and/or non-hydrogenated, ethoxylated and/or propoxylated triglycerides of ricinoleic acid having degree of ethoxylation and/or propoxylation of ≥20, (ii.) addition products of 2-50 mol ethylene oxide on sorbitan monoesters and/or diesters of saturated or unsaturated fatty acids having 6-22 carbon atoms, and (iii.) addition products of 2-50 mol ethylene oxide and 1-20 mol propylene oxide on alpha olefin epoxides having 8-22 carbon atoms and ring-opened with polyols, b. ethoxylated and/or propoxylated glycerol fatty acid monoester and/or diester having degree of ethoxylation of <20, c. polyol selected from glycerol, diglycerol, trigylcerol, tetraglycerol, alkylene glycols and polyalkylene glycols, d. glycerol fatty acid monoester of general formula (I), where $R_1$ is saturated or unsaturated, branched or linear group having 9-19 carbon atoms, and e. ≤20 wt % water. Further described is use of said compositions, and substrates treated with the composition.

13 Claims, No Drawings

US 9,180,075 B2

CONCENTRATES FOR TREATING SUBSTRATES

CROSS-REFERENCE TO RELATED APPLICATIONS

This application is the National Stage entry of PCT/EP2010/006963, filed on Nov. 16, 2010, which claims priority to European Patent application number 09014677.0, filed on Nov. 25, 2009, both of which are incorporated herein by reference in their entireties.

TECHNICAL FIELD

The present invention relates to care and cleansing concentrates, and more particularly to flowable concentrates that can be applied to a substrate.

BACKGROUND

In the field of skin and hair care and cleansing, wet and dry papers or wipes are becoming more and more important. The term "wipes" here includes a very wide variety of substrates such as, for example, nonwovens, tissues and papers.

The generic term "paper or wipe" is understood to cover ca. 3000 different types and articles, some of which can differ considerably in their fields of application and their nature. For their production, a series of additives is required, of which fillers (e.g. chalk or kaolin) and binders (e.g. starch) count among the most important. For the field of tissue and hygiene papers and wipes which are brought into relatively close contact with the human skin, there is a particular need for a pleasant soft feel, which is usually imparted to the paper through careful selection of the fiber materials and in particular a high proportion of fresh groundwood pulp or cellulose.

These papers or wipes can be treated with a very wide variety of impregnation solutions which give the particular paper or wipe its care and/or cleansing properties.

Thus, e.g. DE 10 2005 006 299 A1 describes emulsifier concentrates and their use.

SUMMARY

Embodiments of the present invention are directed toward a composition comprising (a) at least one compound selected from the group consisting of (i.) hydrogenated and/or nonhydrogenated, ethoxylated and/or propoxylated triglycerides of ricinoleic acid with a degree of ethoxylation and/or degree of propoxylation of greater than or equal to 20; (ii.) addition products of from 2 to 50 mol of ethylene oxide onto sorbitan mono- and/or diesters of saturated or unsaturated fatty acids having 6 to 22 carbon atoms; and (iii.) addition products of from 2 to 50 mol of ethylene oxide and 1 to 20 mol of propylene oxide onto alpha-olefin epoxides having 8 to 22 carbon atoms and ring-opened with polyols, (b) at least one ethoxylated and/or propoxylated glycerol fatty acid mono- and/or diester with a degree of ethoxylation of less than 20, (c) at least one polyol selected from the group consisting of glycerol, diglycerol, triglycerol, tetraglycerol, alkylene glycols and polyalkylene glycols, (d) at least one glycerol fatty acid monoester of the general Formula (I) wherein $R_1$ is a saturated or unsaturated, branched or linear radical having 9 to 19 carbon atoms, and (e) less than or equal to 20% by weight of water.

In one or more embodiments, the hydrogenated and/or nonhydrogenated, ethoxylated and/or propoxylated triglycerides of ricinoleic acid (component i.) have a degree of ethoxylation and/or degree of propoxylation of from 20 to 60.

In one or more embodiments, the at least one ethoxylated and/or propoxylated glycerol fatty acid mono- and/or diester (component b) has a degree of ethoxylation of from 3 to 19.

In a specific embodiment, the at least one ethoxylated and/or propoxylated glycerol fatty acid mono- and/or diester (component b) has a degree of ethoxylation of from 3 to 15.

In one or more embodiments, the composition comprises 3 to 50% by weight of at least one component (a), 40 to 90% by weight of at least one component (b), 1 to 10% by weight of at least one component (c), 0.5 to 5% by weight of at least one component (d), and less than or equal to 20% by weight of water.

In one or more embodiments, the composition comprises 5 to 45% by weight of at least on component (a), 50 to 85% by weight of at least one component (b), 2 to 8% by weight of at least one component (c), 1 to 3% by weight of at least one component (d), and less than or equal to 20% by weight of water.

In a specific embodiment, the compositions comprises 10 to 40% by weight of at least one component (a), 55 to 80% by weight of at least one component (b), 4 to 6% by weight of at least one component (c), 1 to 3% of at least one component (d), and less than or equal to 20% by weight of water.

Other embodiments of the present invention are directed to a method of for treating substrates, the method comprising applying a composition to a substrate, followed by optionally drying the substrate, wherein the composition comprises (a) at least one compound selected from the group consisting of (i.) hydrogenated and/or nonhydrogenated, ethoxylated and/or propoxylated triglycerides of ricinoleic acid with a degree of ethoxylation and/or degree of propoxylation of greater than or equal to 20; (ii.) addition products from 2 to 50 mol of ethylene oxide onto sorbitan mono- and/or diesters of saturated or unsaturated fatty acids having 6 to 22 carbon atoms; and (iii.) addition products of from 2 to 50 mol of ethylene oxide and 1 to 20 mol of propylene oxide onto alpha-olefin epoxides having 8 to 22 carbon atoms and ring-opened with polyols, (b) at least one ethoxylated and/or propoxylated glycerol fatty acid mono- and/or diester with a degree of ethoxylation of less than 20, (c) at least one polyol selected from the group consisting of glycerol, diglycerol, triglycerol, tetraglycerol, alkylene glycols and polyalkylene glycols, (d) at least one glycerol fatty acid monoester of general formula (I) where in $R_1$ is a saturated or unsaturated, branched or linear radical having 9 to 19 carbon atoms.

In one or more embodiments, the hydrogenated and/or nonhydrogenated, ethoxylated and/or propoxylated triglycerides of ricinoleic acid (component (i.)) have a degree of ethoxylation and/or degree of propoxylation of from 20 to 60.

In one or more embodiments, the at least one ethoxylated and/or propoxylated glycerol fatty acid mono- and/or diester (component b) has a degree of ethoxylation of from 3 to 19.

In a specific embodiment, the at least one ethoxylated and/or propoxylated glycerol fatty acid mono- and/or diester (component b) has a degree of ethoxylation of from 3 to 15.

Further embodiments of the present invention are direct to a treated substrate obtainable by applying to a substrate at least the following constituents (a) at least one compound selected from the group consisting of (i.) hydrogenated and/or nonhydrogenated, ethoxylated and/or propoxylated triglycerides of ricinoleic acid with a degree of ethoxylation and/or degree of propoxylation of greater than or equal to 20; (ii.) addition products from 2 to 50 mol of ethylene oxide onto sorbitan mono- and/or diesters of saturated or unsaturated fatty acids having 6 to 22 carbon atoms; and (iii.) addition products of from 2 to 50 mol of ethylene oxide and 1 to 20 mol of propylene oxide onto alpha-olefin epoxides having 8 to 22 carbon atoms and ring-opened with polyols, (b) at least one ethoxylated and/or propoxylated glycerol fatty acid mono- and/or diester with a degree of ethoxylation of less than 20, (c) at least one polyol selected from the group consisting of glycerol, diglycerol, triglycerol, tetraglycerol, alkylene glycols and polyalkylene glycols, (d) at least one glycerol fatty acid monoester of the general formula (I) wherein $R_1$ is a saturated or unsaturated, branched or linear radical having 9 to 19 carbon atoms.

In one or more embodiments, the hydrogenated and/or nonhydrogenated, ethoxylated and/or propoxylated triglycerides of ricinoleic acid (component (i.)) have a degree of ethoxylation and/or degree of propoxylation of from 20 to 60.

In one or more embodiments, the at least one ethoxylated and/or propoxylated glycerol fatty acid mono- and/or diester (component b) has a degree of ethoxylation of from 3 to 19.

In a specific embodiment, the at least one ethoxylated and/or propoxylated glycerol fatty acid mono- and/or diester (component b) has a degree of ethoxylation of from 3 to 15.

In one or more embodiments, the treated substrate is obtainable by applying to a substrate a composition, wherein the composition comprises at least the following constituents: (a) at least one compound selected from the group consisting of (i.) hydrogenated and/or nonhydrogenated, ethoxylated and/or propoxylated triglycerides of ricinoleic acid with a degree of ethoxylation and/or degree of propoxylation of greater than or equal to 20; (ii.) addition products from 2 to 50 mol of ethylene oxide onto sorbitan mono- and/or diesters of saturated or unsaturated fatty acids having 6 to 22 carbon atoms; and (iii.) addition products of from 2 to 50 mol of ethylene oxide and 1 to 20 mol of propylene oxide onto alpha-olefin epoxides having 8 to 22 carbon atoms and ring-opened with polyols, (b) at least one ethoxylated and/or propoxylated glycerol fatty acid mono- and/or diester with a degree of ethoxylation of less than 20, (c) at least one polyol selected from the group consisting of glycerol, diglycerol, triglycerol, tetraglycerol, alkylene glycols and polyalkylene glycols, (d) at least one glycerol fatty acid monoester of the general formula (I) wherein $R_1$ is a saturated or unsaturated, branched or linear radical having 9 to 19 carbon atoms.

In one or more embodiments, the hydrogenated and/or nonhydrogenated, ethoxylated and/or propoxylated triglycerides of ricinoleic acid (component (i.)) have a degree of ethoxylation and/or degree of propoxylation of from 20 to 60.

In one or more embodiments, the at least one ethoxylated and/or propoxylated glycerol fatty acid mono- and/or diester (component b) has a degree of ethoxylation of from 3 to 19.

In a specific embodiment, the at least one ethoxylated and/or propoxylated glycerol fatty acid mono- and/or diester (component b) has a degree of ethoxylation of from 3 to 15.

Still further embodiments of the present invention are directed to a method of cleansing and/or caring for skin and hair, the method comprising using the treated substrate of the present invention to cleanse and/or care for skin and hair.

DETAILED DESCRIPTION

The present invention provides a composition which is flowable at standard temperature and is thus easy to pump. At the same time, this composition is stable, i.e. no separation of the constituents should take place. Furthermore, it was desirable that these compositions exhibit no phase separation following dilution with water (and optionally further cosmetic ingredients, in particular with lipophilic components), the stability over a prolonged period at elevated temperatures being of particular interest here. It was also of interest that these compositions can be diluted with low energy expenditure.

Furthermore, the compositions have good sensory properties and/or impart advantageous sensory properties to the substrate to which they are applied, the softness of the substrate treated with the composition being particularly of interest here. Provided also are compositions which make it possible to apply further constituents, in particular oil-soluble constituents, to the substrate. The present invention also provides substrates which permit a skin-gentle cleansing of the skin and at the same time have a high skin compatibility. In particular, the refatting and also the moisture binding of the skin were of interest here.

Provided are compositions comprising
a. at least one compound selected from the group consisting of
  i. hydrogenated and/or nonhydrogenated, ethoxylated and/or propoxylated triglycerides of ricinoleic acid with a degree of ethoxylation and/or degree of propoxylation of greater than or equal to 20, in particular from 20 to 60,
  ii. addition products of from 2 to 50 mol of ethylene oxide onto sorbitan mono- and/or diesters of saturated or unsaturated fatty acids having 6 to 22 carbon atoms, and
  iii. addition products of from 2 to 50 mol of ethylene oxide and 1 to 20 mol of propylene oxide onto alpha-olefin epoxides having 8 to 22 carbon atoms and ring-opened with polyols,
b. at least one ethoxylated and/or propoxylated glycerol fatty acid mono- and/or diester with a degree of ethoxylation of less than 20, preferably 3 to 19, in particular 3 to 15,
c. at least one polyol different from components a, b and d,
d. at least one glycerol fatty acid monoester of the general formula (I)

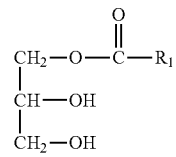

in which $R_1$ is a saturated or unsaturated, branched or linear radical having 9 to 19 carbon atoms,
e. less than or equal to 20% by weight of water.

In one or more embodiments, the invention relates to compositions comprising
a. at least one compound selected from the group consisting of
  i. hydrogenated and/or nonhydrogenated, ethoxylated and/or propoxylated triglycerides of ricinoleic acid with a degree of ethoxylation and/or degree of propoxylation of greater than or equal to 20, in particular from 20 to 60,
  ii. addition products of from 2 to 50 mol of ethylene oxide onto sorbitan mono- and/or diesters of saturated or unsaturated fatty acids having 6 to 22 carbon atoms, and
  iii. addition products of from 2 to 50 mol of ethylene oxide and 1 to 20 mol of propylene oxide onto alpha-olefin epoxides having 8 to 22 carbon atoms and ring-opened with polyols,
b. at least one ethoxylated and/or propoxylated glycerol fatty acid mono- and/or diester with a degree of ethoxylation of less than 20, preferably 3 to 19, in particular 3 to 15, c. at least one polyol selected from the group consisting of glycerol, diglycerol, triglycerol, tetraglycerol, alkylene glycols and polyalkylene glycols,
d. at least one glycerol fatty acid monoester of the general formula (I)

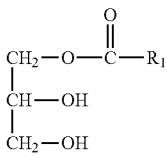

in which $R_1$ is a saturated or unsaturated, branched or linear radical having 9 to 19 carbon atoms,
e. less than or equal to 20% by weight of water.

The compositions according to the invention are flowable. Flowable is the term used to refer to those compositions whose viscosity is below 20 Pas (Brookfield rotary viscometer, RVF, spindle TE, 4 rpm, 23° C.). In one or more embodiments, the compositions are thin-liquid. Thin-liquid is the term used to refer to those compositions whose viscosity is less than or equal to 800 mPas (Brookfield RVF 23° C., spindle 5, 10 rpm).

All % by weight data refer to the total weight of the composition.

In one or more embodiments, the composition comprises no ethoxylated emulsifiers with an HLB value of less than 6.

Component (a)

The compositions comprise, as component (a), at least one compound selected from the group consisting of
i. hydrogenated and/or nonhydrogenated, ethoxylated and/or propoxylated triglycerides of ricinoleic acid with a degree of ethoxylation and/or degree of propoxylation of greater than or equal to 20, in particular from 20 to 60,
ii. addition products of from 2 to 50 mol of ethylene oxide onto sorbitan mono- and/or diesters of saturated or unsaturated fatty acids having 6 to 22 carbon atoms, and
iii. addition products of from 2 to 50 mol of ethylene oxide and 1 to 20 mol of propylene oxide onto alpha-olefin epoxides having 8 to 22 carbon atoms and ring-opened with polyols.

Component (i.)

Suitable components (a) are ethoxylated and/or propoxylated triglycerides of ricinoleic acid with a degree of ethoxylation and/or degree of propoxylation of greater than or equal to 20, in particular from 20 to 60. These compounds can be hydrogenated and/or nonhydrogenated.

The ethoxylated triglycerides of ricinoleic acid conform to the general formula:

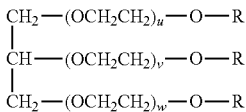

where
u, v and w, independently of one another, are a number from 0 to 100, and
the sum of u, v and w is greater than or equal to 20, preferably 20 to 60, and
R is the acyl radical of the ricinoleic acid [(R)-12-hydroxy-(Z)-octadec-9-enoic acid].

The propoxylated triglycerides of ricinoleic acid conform to the following formula:

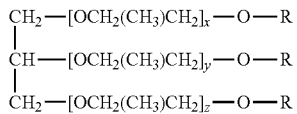

where
x, y and z, independently of one another, are a number from 0 to 100, and
the sum of x, y and z is greater than or equal to 20, preferably 20 to 60, and
R is the acyl radical of the ricinoleic acid [(R)-12-hydroxy-(Z)-octadec-9-enoic acid].

Also of suitability according to the invention are triglycerides of ricinoleic acid which have been ethoxylated and propoxylated:

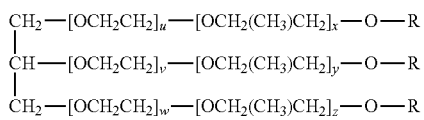

where
u, v, w, x, y and z, independently of one another, are a number from 0 to 100, and
the sum of u, v, w, x, y and z is greater than or equal to 20, preferably 20 to 60, and
R is the acyl radical of the ricinoleic acid [(R)-12-hydroxy-(Z)-octadec-9-enoic acid].

The order of the ethylene oxide and propylene oxide units in the ethoxylated and propoxylated triglycerides of the ricinoleic acid depends here on the conditions chosen during the preparation.

In the hydrogenated or partially hydrogenated (ethoxylated and/or propoxylated) triglycerides obtainable by hydrogenation, the double bonds in the acyl radicals of the ricinoleic acid are completely or partly saturated.

As component (a), it is possible to use either ethoxylated or propoxylated or the respective corresponding hydrogenated compounds individually or in mixtures with one another.

The degree of ethoxylation or propoxylation indicates the average moles of ethylene oxide or propylene oxide units, and thus corresponds to the sum of u, v, w, x, y and z.

The triglycerides of the ricinoleic acid suitable according to the invention as components (i.) are present e.g. as the main constituent in commercially available ethoxylated ricinus oils or propoxylated ricinus oils. These are commercially available for example under the following INCI names (in brackets in each case the trade name and manufacturer):
INCI: PEG-20 Castor Oil (Nikkol CO-20TX, Nikko Chemical Co.)
INCI: PEG-20 Hydrogenated Castor Oil (Nikkol HCO-20, Nikko Chemical Co.)
INCI: PEG-40 Hydrogenated Castor Oil (Eumulgin®HRE 40, Cognis GmbH; Cremophor RH 40, BASF Corp.; Tagat CH 40, Evonik Goldschmidt Corp.),
INCI: PEG-60 Hydrogenated Castor Oil (Eumulgin®HRE 60, Cognis GmbH; Cremophor RH 60, BASF Corp.; Tagat CH 60, Evonik Goldschmidt Corp.; Croduret 60, Croda Europe)

INCI: PEG-40 Castor Oil (Eumulgin® RO 40, Cognis GmbH; Etocas 40, Croda Europe; Nikkol CO-40TX, Nikko Chemical Co.)

INCI: PEG-60 Castor Oil (trade name Nikkol CO-60TX, Nikko Chemical Co.)

INCI: PEG-80 Hydrogenated Castor Oil (tradename Nikkol HCO-80, Nikko Chemical Co.)

INCI: PEG-100 Hydrogenated Castor Oil (trade name Nikkol HCO-100, Nikko Chemical Co.)

Component (ii.)

Further suitable components (a) are addition products of from 2 to 50 mol of ethylene oxide onto sorbitan mono- and/or diesters of saturated or unsaturated fatty acids having 6 to 22 carbon atoms.

In a preferred embodiment, addition products of from 2 to 50 mol of ethylene oxide onto sorbitan mono- and/or diesters of saturated and linear fatty acids having 6 to 22 carbon atoms are used.

Sorbitan is the collective name for 4-valent alcohols which are formed by removing 1 mol of water from D-glucitol (sorbitol) by heating under the catalytic influence of acids. Esterification with fatty acids produces the corresponding sorbitan esters (1,4-sorbitan esters and 1,5-sorbitan esters).

Sorbitan monoesters suitable according to the invention are, for example, compounds of the following formula (ethoxylated 1,4-sorbitan monoesters):

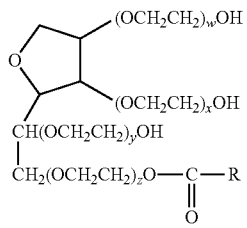

in which R is a saturated or unsaturated, linear or branched radical having 5 to 21 carbon atoms, in which w, x, y and z, independently of one another, are numbers from 0 to 50, where the sum of w, x, y and z is 2 to 50.

In one or more embodiments, compounds of this formula comprise R, which is a linear and saturated radical having 11 to 17 carbon atoms.

In one or more embodiments, for compounds of this formula, the sum of w, x, y, and z is 4 to 40.

Typical examples of ethoxylated sorbitan esters suitable according to the invention are the products obtainable under the INCI name Polysorbate 20 (trade name Eumulgin®SML 20, Cognis GmbH). Polysorbate 20 is a mixture of primarily sorbitan monoesters of the following formula in which the sum of w+x+y+z is on average 20.

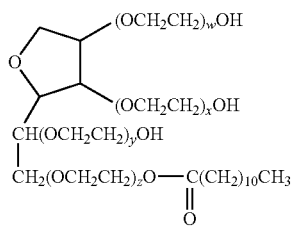

Further suitable ethoxylated sorbitan esters are the products available under the INCI name Polysorbate 21 (trade name Tween 21, Croda), in which the sum of w+x+y+z is on average 4.

Also suitable, for example, are the products available under the INCI name Polysorbate 40 (trade name Tween 40, Croda). Polysorbate 40 is a mixture of predominantly sorbitan monoesters of the following formula in which the sum of w+x+y+z is on average 20.

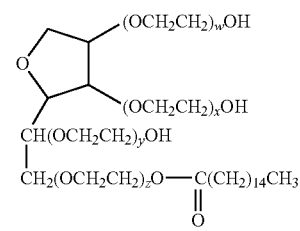

Component (iii.)

Further suitable components (a) are addition products of from 2 to 50 mol of ethylene oxide and 1 to 20 mol of propylene oxide onto alpha-olefin epoxides having 8 to 22 carbon atoms and ring-opened with polyols.

Alpha-olefin epoxides having 8 to 22 carbon atoms are compounds which carry an epoxide group in the terminal position and conform to the general formula:

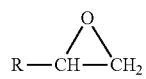

in which R is a radical having 6 to 20 carbon atoms.

The components (a) are obtained by ring-opening of alpha-olefin epoxides having 8 to 22 carbon atoms by polyols and subsequent propoxylation and ethoxylation (or subsequent ethoxylation and propoxylation). The polyols which are used for the ring opening are preferably alkylene glycols or polyethylene glycols, in particular ethylene glycol.

In one or more embodiments, a compound which is obtained by ring-opening of alpha-olefin epoxides having 8 to 22 carbon atoms, preferably of alpha-olefin epoxides having 8 to 16, preferably having 12 to 16, carbon atoms is used as component (a).

In one or more embodiments, a compound which is obtained by ring-opening of alpha-olefin epoxides with ethylene glycol is used as component (a).

These compounds conform to the general formula (I) and/or (II):

R—CH(OH)—CH$_2$—O—CH$_2$—CH$_2$—O—[CH(CH$_3$)CH$_2$—O]$_m$—[CH$_2$—CH$_2$—O]$_n$—H    (I)

in which
m is a number from 1 to 20, preferably a number from 1 to 5,
n is a number from 2 to 50, preferably a number from 5 to 30, in particular a number from 8 to 25,
R is a radical having 6 to 20 carbon atoms, preferably 10 to 14 carbon atoms, R—CH{—O[CH(—CH$_3$)CH$_2$—O]$_p$—[CH$_2$—CH$_2$—O]$_o$—H]}—CH$_2$—O—CH$_2$—CH$_2$—O—[CH(CH$_3$)CH$_2$—O]$_m$—[CH$_2$—CH$_2$—O]$_n$—H    (II)

in which
the sum of m and p is 1 to 20, preferably 1 to 5,
the sum of n and o is 2 to 50, preferably a 5 to 30, in particular a number from 8 to 25, R is a radical having 6 to 20 carbon atoms, preferably 10 to 14 carbon atoms.

The order of the ethylene oxide and propylene oxide units here depends on the reaction conditions selected during the preparation. In one or more embodiments, after ring-opening the epoxide, firstly a propoxylation and then an ethoxylation is carried out. These compounds conform to the formulae (I) and/or (II). If firstly an ethoxylation and then a propoxylation is carried out, the order of the ethoxy and propoxy units in the formulae (I) and (II) is accordingly swapped.

In one or more embodiments, the composition comprises compounds of the general formula (I) and/or (II) in which R is a radical having 10 carbon to 14 carbon atoms, m and p=1, n and o=9. Such compounds are commercially available under the INCI name PPG-1-PEG-9 Laurylglycol ether (Eumulgin® L, Cognis GmbH).

Amount of (a)

In one or more embodiments, the compositions comprise 3 to 50, in particular 5 to 45, preferably 10 to 40, in particular 20 to 30, % by weight—based on the total weight of the composition—of component (a).

Ratio of Component (b) to (a)

In one or more embodiments, the weight ratio of component (b) to (a) is greater than or equal to 1, preferably greater than or equal to 1.5, in particular greater than or equal to 2. Preferably, the weight ratio of (b) to (a) is greater than or equal to 5, in particular greater than or equal to 7, preferably greater than or equal to 10.

Component (b)

As component (b), the compositions comprise at least one ethoxylated and/or propoxylated glycerol fatty acid mono- and/or diester with a degree of ethoxylation and/or propoxylation of less than 20, preferably of 3 to 19, in particular 3 to 15.

As component (b), the compositions can comprise either one ethoxylated and/or propoxylated glycerol fatty acid mono- and/or diester with a degree of ethoxylation and/or propoxylation of less than 20, or a mixture of two or more ethoxylated and/or propoxylated fatty acid mono- and/or diesters with a degree of ethoxylation and/or propoxylation of less than 20.

Ethoxylated and/or propoxylated glycerol fatty acid mono- and/or diesters with a degree of ethoxylation and/or propoxylation of less than 20 conforming to the general formula:

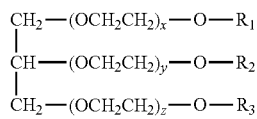

where x, y and z, independently of one another, are a number from 0 to 19, the sum of x, y and z is 1 to 19, preferably 3 to 19, in particular 5 to 15, $R_1$, $R_2$ and $R_3$, independently of one another, are selected from hydrogen, a saturated or unsaturated, linear or branched acyl radical having 8 to 22 carbon atoms, and at least one radical $R_1$, $R_2$ or $R_3$ is hydrogen.

Corresponding propoxylated glycerol fatty acid mono- and/or diesters with a degree of propoxylation of less than 20 conform to the following general formula:

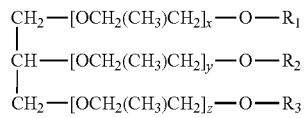

where x, y and z, independently of one another, are a number from 0 to 19, the sum of x, y and z is 1 to 19, preferably 3 to 19, in particular 5 to 15, $R_1$, $R_2$ and $R_3$, independently of one another, are selected from hydrogen, a saturated or unsaturated, linear or branched acyl radical having 8 to 22 carbon atoms, and at least one radical $R_1$, $R_2$ or $R_3$ is hydrogen.

Examples of suitable acyl radicals $R_1$, $R_2$ or $R_3$ are $C(=O)[CH_2]_{16}$—$CH_3$ (=octadecanoyl radical, =stearoyl radical)

—$C(=O)$—$[CH_2]_{14}$—$CH_3$ (=hexanedecanoyl radical, =palmitoyl radical)

—$C(=O)$—$[CH_2]_{12}$—$CH_3$ (=tetradecanoyl radical, =myristoyl radical)

—$C(=O)$—$[CH_2]_{10}$—$CH_3$ (=dodecanoyl radical, =lauroyl radical)

—$C(=O)$—$[CH_2]_8$—$CH_3$ (=decanoyl radical)

—$C(=O)$—$[CH_2]_6$—$CH_3$ (=octanoyl radical)

Likewise of suitability are glycerol fatty acid monoesters and glycerol fatty acid diesters which are both ethoxylated and propoxylated.

As component (b), it is possible to use either glycerol fatty acid monoesters, glycerol fatty acid diesters or mixtures of monoesters and diesters. The ethoxylated/propoxylated glycerol fatty acid esters preferably used according to the invention are generally mixtures of glycerol fatty acid monoesters and glycerol fatty acid diesters.

In one or more embodiments, components (b) are a compound selected from the group which is formed from Polyoxyethylene(10) olive glycerides (INCI: PEG-10 Olive Glycerides), Polyoxyethylene(11) avocado glycerides (INCI: PEG-11 Avocado Glycerides, CAS: 103819-44-9), Polyoxyethylene(11) cocoa butter glycerides (INCI: PEG-11 Cocoa Butter Glycerides), Polyoxyethylene(9) coconut glycerides (INCI: PEG-9 Cocoglycerides, CAS: 67762-35-0), Mono-, di- and trihydrogenated palm kernel glyceride PEG-6 complex (INCI: Hydrogenated Palm Kernel Glycerides PEG-6 Esters), Polyoxyethylene(7) glyceryl monococoate (CAS: 66105-29-1 and 68201-46-7) and Polyoxyethylene(6) caprylic/capric glyceride (INCI: PEG-6 Caprylic/Capric Glycerides).

In a specific embodiment, component (b) is selected from polyoxyethylene(7) glyceryl monococoate (CAS: 66105-29-1 and 68201-46-7), polyoxyethylene(6) caprylic/capric glyceride (INCI: PEG-6 Caprylic/Capric Glycerides) and polyoxyethylene(9) coconut glycerides (INCI: PEG-9 Cocoglycerides, CAS: 67762-35-0).

Amount of (b)

In one or more embodiments, the compositions comprise 40 to 90, in particular 50 to 85, preferably 55 to 80% by weight—based on the total weight of the composition—of component (b).

Component (c)

The compositions comprise at least one polyol as component (c). Component (c) here is a component different from the components (a), (b) and (d).

Within the context of the invention, polyols are understood as meaning substances which carry at least two alcoholic hydroxyl groups in the molecule. The polyols used are preferably compounds which carry 2 to 15 carbon atoms and at least 2 hydroxyl groups. Polyols which can be used are compounds which carry 3 to 15 carbon atoms and at least three hydroxyl groups.

In one or more embodiments, the polyols contain no further elements apart from oxygen, hydrogen and carbon. The compositions can comprise both a polyol and also a mixture of two or more polyols as component (c).

In one embodiment of the invention, the polyols (c) are selected from the group consisting of glycerol, diglycerol, triglycerol, tetraglycerol, alkylene glycols and polyalkylene glycols.

Suitable alkylene glycols are ethylene glycol (=1,2-ethanediol), diethylene glycol (=2,2'-oxydiethanol; HO—(CH$_2$)$_2$—O—(CH$_2$)$_2$—OH), triethylene glycol (=2,2'-(ethylenedioxy)diethanol), 1,2-propylene glycol, 1,3-propylene glycol, butylene glycols (=butanediols) such as 1,2-butylene glycol, 1,3-butylene glycol, 1,4-butylene glycol, 2,3-butylene glycol; pentane-1,5-diol; pentane-1,2-diol; meso-pentane-2,4-diol, (2R,4R)-pentane-2,4-diol; (2S,4S)-pentane-2,4-diol, hexanediols, such as, for example, hexylene glycol (=2-methylpentane-2,4-diol), heptanediols, octanediols and decanediols.

Polyalkylene glycols is the term used to refer to predominantly linear, but sometimes also branched polyethers which are formed from the polycondensation of glycols. The technically important representatives of these polyether polyols are the polyethylene glycols, polypropylene glycols, polyethylene/polypropylene glycols, and polytetramethylene glycols and analogous compounds thereof which are prepared by ring-opening polymerization of ethylene oxide, propylene oxide and tetrahydrofuran.

Within the context of the invention, particularly preferred polyalkylene glycols are polyethylene glycols and/or polypropylene glycols and/or polyethylene-polypropylene glycols with an average molecular weight of from 100 to 1000 daltons.

The preferred polyalkylene glycols conforming here to the general formula

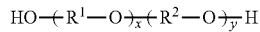

If R$^1$ and R$^2$=(CH$_2$)$_2$, the formula refers to poly-ethylene glycols, if R$^1$ and R$^2$=CH$_2$—CH(CH$_3$), the formula refers to polypropylene glycols. If R$^1$=(CH$_2$)$_2$ and R$^2$=CH$_2$—CH(CH$_3$), the formula refers to poly-ethylene/polypropylene glycols.

These compounds are commercially available for example under the INCI name (trade name and manufacturer in parentheses):

INCI: PEG-4 (Polyglykol 200 USP, Clariant International; Pluracare E 200, BASF Corp.)
INCI: PEG-12 (Polyglykol 600, Clariant International; Pluracare E 600, BASF Corp.)
INCI: PPG-3 (Newpol PP-200, Sanyo Chemical Industries)

In a further embodiment of the invention, the polyols (c) are selected from the group which is formed from glycerol, diglycerol, triglycerol, tetraglycerol alkylene glycols selected from the group consisting of ethylene glycol (=1,2-ethanediol), diethylene glycol (=2,2'-oxydiethanol; HO—(CH$_2$)$_2$—O—(CH$_2$)$_2$—OH), triethylene glycol (=2,2'-(ethylenedioxy)diethanol), 1,2-propylene glycol, 1,3-propylene glycol, butylene glycols (=butanediols) such as 1,2-butylene glycol, 1,3-butylene glycol, 1,4-butylene glycol, 2,3-butylene glycol; pentane-1,5-diol; pentane-1,2-diol; meso-pentane-2,4-diol, (2R,4R)-pentane-2,4-diol; (2S,4S)-pentane-2,4-diol, hexanediols, such as, for example, hexylene glycol (=2-methylpentane-2,4-diol), heptanediols, octanediols and decanediols.

Polyalkylene glycols with an average molecular weight of from 100 to 1000 daltons Technical-grade oligoglycerol mixtures with a degree of intrinsic condensation of from 1.5 to 10, such as, for example, technical-grade diglycerol mixtures with a diglycerol content of from 40 to 50% by weight;

methylol compounds, such as in particular trimethylolethane, trimethylolpropane, trimethylolbutane, pentaerythritol and dipentaerythritol;

short-chain alkyl glucosides, in particular those having 1 to 8 carbon atoms in the alkyl radical, such as, for example, methyl and butyl glucoside;

sugar alcohols having 5 to 12 carbon atoms, such as, for example, sorbitol or mannitol, sugars having 5 to 12 carbon atoms, such as, for example, glucose or sucrose;

amino sugars, such as, for example, glucamine;

dialcohol amines, such as diethanolamine or 2-amino-1,3-propanediol.

Amount of (c)

In one or more embodiments, the compositions comprise 1 to 10, in particular 2 to 8, preferably 3 to 6% by weight—based on the total weight of the composition—of component (c).

Component (d)

As component (d), the compositions comprise at least one glycerol fatty acid monoester of the general formula

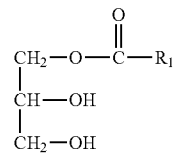

in which R$_1$ is a saturated or unsaturated, branched or linear radical having 9 to 19 carbon atoms. Preferably, R is a linear radical, preferably R is a saturated radical (alkyl radical).

Examples of suitable glycerol fatty acid monoesters according to formula (I) are glyceryl laurate [commercially available as Monomuls® 90-L 12, Cognis GmbH], glyceryl myristate, glyceryl stearate, glyceryl oleate [commercially available as Monomuls® 90-O 18, Cognis GmbH], glyceryl palmitate, glyceryl palmitoleate, glyceryl cocoate, glyceryl linoloate.

In one or more embodiments, glyceryl oleate and/or glyceryl laurate (R$_1$=$_n$C$_{11}$H$_{23}$) is used as glycerol fatty acid monoester.

As component (d), the compositions according to the invention can comprise either one glycerol fatty acid monoester or a mixture of two or more glycerol fatty acid monoesters.

Amount of (d)

In a preferred embodiment of the invention, the compositions comprise 0.5 to 5, in particular 1 to 3% by weight—based on the total weight of the composition—of component (d).

Component (e)

The compositions according to the invention, such as, for example, the compositions according to claim 1 and/or 2, are "concentrates", i.e. the compositions comprise less than or equal to 20, in particular less than or equal to 15, preferably less than or equal to 10, in particular less than or equal to 5% by weight of water, based on the total weight of the composition.

In a specific embodiment of the invention, the composition comprises no added water and the water present in the composition originates exclusively from the residual water of components (a) to (d). In this case, the water content of the compositions is usually below 3% by weight, in particular below 1% by weight, based on the total weight of the composition.

One or more embodiments relates to a composition comprising
- 3 to 50, in particular 5 to 45, preferably 10 to 40% by weight of at least one component (a)
- 40 to 90, in particular 50 to 85, preferably 55 to 80% by weight of at least one component (b)
- 1 to 10, in particular 2 to 8, preferably 3 to 6% by weight of at least one component (c)
- 0.5 to 5, in particular 2 to 8, preferably 3 to 6% by weight of at least one component (d)
- less than or equal to 20% by weight of water.

All weight data refer to the total weight of the composition.

The invention further provides the use of compositions which comprises at least the following constituents:
a. at least one compound selected from the group consisting of
   i. hydrogenated and/or nonhydrogenated, ethoxylated and/or propoxylated triglycerides of ricinoleic acid with a degree of ethoxylation and/or degree of propoxylation of greater than or equal to 20, in particular from 20 to 60,
   ii. addition products of from 2 to 50 mol of ethylene oxide onto sorbitan mono- and/or diesters of saturated or unsaturated fatty acids having 6 to 22 carbon atoms, and
   iii. addition products of from 2 to 50 mol of ethylene oxide and 1 to 20 mol of propylene oxide onto alpha-olefin epoxides having 8 to 22 carbon atoms and ring-opened with polyols,
b. at least one ethoxylated and/or propoxylated glycerol fatty acid mono- and/or diester with a degree of ethoxylation of less than 20, preferably 3 to 19, in particular 3 to 15,
c. at least one polyol different from the constituents a, b and d, preferably a polyol selected from the group consisting of glycerol, diglycerol, triglycerol, tetraglycerol, alkylene glycols and polyalkylene glycols,
d. at least one glycerol fatty acid monoester of the general formula (I)

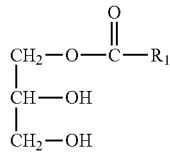

in which $R_1$ is a saturated or unsaturated, branched or linear radical having 9 to 19 carbon atoms, for treating substrates.

In one embodiment, a composition according to the invention, optionally following dilution with water and/or further constituents, is used for treating substrates.

The term treating here involves any way of applying a composition to at least one side of the substrate. Of suitability for this purpose are all relevant known methods, with the help of which liquids can be applied to more or less solid surfaces. By way of example, mention may be made of: impregnation, saturation, coating, spraying (on), immersion, finishing, scraping etc. The treatment can be carried out here at room temperature or under the action of heat. The application of the compositions can be followed by a short drying step.

The compositions and in particular the concentrates impart advantageous care and/or sensory properties to the substrates treated with them. In particular, the compositions and especially the concentrates impart refatting and moisturizing properties to the substrates treated with them. Using the compositions and especially using the concentrates, it is also possible to apply further oil-soluble substances to the substrates.

The invention further provides a method for treating substrates, in which a composition which comprises at least the following constituents:
a. at least one compound selected from the group consisting of
   i. hydrogenated and/or nonhydrogenated, ethoxylated and/or propoxylated triglycerides of ricinoleic acid with a degree of ethoxylation and/or degree of propoxylation of greater than or equal to 20, in particular from 20 to 60,
   ii. addition products of from 2 to 50 mol of ethylene oxide onto sorbitan mono- and/or diesters of saturated or unsaturated fatty acids having 6 to 22 carbon atoms, and
   iii. addition products of from 2 to 50 mol of ethylene oxide and 1 to 20 mol of propylene oxide onto alpha-olefin epoxides having 8 to 22 carbon atoms and ring-opened with polyols,
b. at least one ethoxylated and/or propoxylated glycerol fatty acid mono- and/or diester with a degree of ethoxylation of less than 20, preferably 3 to 19, in particular 3 to 15,
c. at least one polyol different from the constituents a, b and d, preferably a polyol selected from the group consisting of glycerol, diglycerol, triglycerol, tetraglycerol, alkylene glycols and polyalkylene glycols,
d. at least one glycerol fatty acid monoester of the general formula (I)

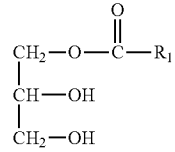

in which $R_1$ is a saturated or unsaturated, branched or linear radical having 9 to 19 carbon atoms, is applied to a substrate and this is optionally dried.

The invention further provides a method for treating substrates in which a composition according to the invention, optionally after dilution with water and further constituents, is applied to a substrate and this is optionally dried.

The compositions according to the invention can be applied neat to the substrate, but they are usually diluted. In the simplest case, the dilution takes place with water, the composition according to the invention usually being used in amounts of 0.5-8.0% by weight, preferably 0.5-5.0% by weight, in particular 0.5-3.0% by weight, based on the total weight of the dilution.

The invention further provides a treated substrate obtainable by applying to a substrate at least the following constituents:

a. at least one compound selected from the group consisting of
   i. hydrogenated and/or nonhydrogenated, ethoxylated and/or propoxylated triglycerides of ricinoleic acid with a degree of ethoxylation and/or degree of propoxylation of greater than or equal to 20, in particular from 20 to 60,
   ii. addition products of from 2 to 50 mol of ethylene oxide onto sorbitan mono- and/or diesters of saturated or unsaturated fatty acids having 6 to 22 carbon atoms, and
   iii. addition products of from 2 to 50 mol of ethylene oxide and 1 to 20 mol of propylene oxide onto alpha-olefin epoxides having 8 to 22 carbon atoms and ring-opened with polyols,
b. at least one ethoxylated and/or propoxylated glycerol fatty acid mono- and/or diester with a degree of ethoxylation of less than 20, preferably 3 to 19, in particular 3 to 15,
c. at least one polyol different from the constituents a, b and d, preferably a polyol selected from the group consisting of glycerol, diglycerol, triglycerol, tetraglycerol, alkylene glycols and polyalkylene glycols,
d. at least one glycerol fatty acid monoester of the general formula (I)

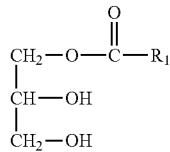

in which $R_1$ is a saturated or unsaturated, branched or linear radical having 9 to 19 carbon atoms.

The constituents here can be applied to the substrate individually or in any desired combinations. In a preferred embodiment of the invention, the constituents are provided in the form of a composition and the substrate is treated with this composition. In one or more embodiments, a composition according to the invention is provided and, directly or following dilution with water and optionally further constituents, is applied to the substrate. This may be followed with a drying step.

The invention further provides a treated substrate obtainable by applying to a substrate a composition, where the composition comprises at least the following constituents:

a. at least one compound selected from the group consisting of
   i. hydrogenated and/or nonhydrogenated, ethoxylated and/or propoxylated triglycerides of ricinoleic acid with a degree of ethoxylation and/or degree of propoxylation of greater than or equal to 20, in particular from 20 to 60,
   ii. addition products of from 2 to 50 mol of ethylene oxide onto sorbitan mono- and/or diesters of saturated or unsaturated fatty acids having 6 to 22 carbon atoms, and
   iii. addition products of from 2 to 50 mol of ethylene oxide and 1 to 20 mol of propylene oxide onto alpha-olefin epoxides having 8 to 22 carbon atoms and ring-opened with polyols,
b. at least one ethoxylated and/or propoxylated glycerol fatty acid mono- and/or diester with a degree of ethoxylation of less than 20, preferably 3 to 19, in particular 3 to 15,
c. at least one polyol different from the constituents a, b and d, preferably a polyol selected from the group consisting of glycerol, diglycerol, triglycerol, tetraglycerol, alkylene glycols and polyalkylene glycols,
d. at least one glycerol fatty acid monoester of the general formula (I)

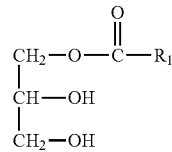

in which $R_1$ is a saturated or unsaturated, branched or linear radical having 9 to 19 carbon atoms.

The invention further provides a treated substrate obtainable by applying a composition according to the invention to a substrate.

The constituents and compositions impart advantageous care and/or sensory properties to the substrates treated with them. In particular, they impart refatting and moisturizing properties to the substrates treated with them. The substrates treated in this way exhibit advantageous properties particularly with regard to their softness compared with prior art substrates.

The substrates treated according to the invention can be used for example as care or cleansing wipes.

In this connection, both applications in the field of skincare or cleansing (in particular babycare or cleansing) are possible. For example, mention may be made of care or cleansing wipes for the facial skin (so-called facial tissues, make-up removing wipes etc.), freshening wipes for the skin, antibacterial and/or deodorizing wipes, products for intimate care (such as, for example, tampons, sanitary napkins, panty liners, intimate care wipes), dry or moist toilet paper, incontinence products, self-tanning wipes or so-called insect repellent wipes. Using the compositions according to the invention, it is possible to apply the constituents required for the particular application (e.g. deodorizing active ingredients or oil-soluble care components) to the substrate. The substrates treated in this way are also suitable for the disinfection of skin and hair.

Accordingly, perfumes, further oils, preservatives, UV light protection factors, biogenic active ingredients and actives such as e.g. dihydroxyacetone, insect repellents, antiinflammatory active ingredients (e.g. for baby wipes) or disinfectants can also be added to the compositions and to their dilutions. The type and amounts of the particular additives are governed by the intended use.

The invention therefore further provides the use of a treated substrate for the cleansing and/or care of skin and hair.

The invention therefore further provides the use of a treated substrate for the disinfection of skin and hair.

Suitable substrates are in principle any carrier which allows the composition or its constituents to absorb. Within the context of the invention, parts of the human body are not a substrate. Suitable substrates are, for example, tissue papers and/or tissue fabric and/or tissue wipes (referred to hereinbelow as tissue wipes). These can be constructed from one or more layers. As a rule, the papers have a weight per square meter of from to 65, preferably 15 to 30 g and a density of 0.6 g/cm and less. Examples of tissue papers are toilet papers, paper pocket wipes, face cleansing wipes, make-up removal wipes, freshening wipes, household wipes and the like. Besides the paper-based tissues, corresponding tissue fabrics which are produced from fiber material or fleece material are also contemplated.

According to the invention, multilayered tissue wipes are preferred as substrate. In particular, preference is given to those tissue wipes which have an impermeable and/or partly permeable barrier between the individual layers. The partly permeable barrier can be formed for example as a semipermeable membrane. With wipes of this type, two or more compositions (optionally after prior dilution) can be applied to one wipe. This can be very particularly preferred in order to bring about cleansing with one side of the wipe by means of the composition applied to the wipe. The other side can then be used for example for rubbing for the purposes of drying or optionally for applying a care active ingredient to the skin.

Furthermore, according to the invention, it may be very particularly preferred if the wipes consist of at least layers of tissue wipes treated with compositions (optionally after prior dilution). Advantageously, in each case 1 layer of wipe is then formed as a semipermeable membrane between at least 2 layers of treated wipe. The semipermeable membrane here is permeable in the direction of the outer wipe layers. As a result, in the inside, for example, a composition (optionally after prior dilution) can be applied to the innermost layer which is either immiscible and/or not stable with the composition applied to the outer side. Consequently, it is possible to offer "two in one wipes" for cleansing and care. The invention of course encompasses the different color configuration of the wipe layers. Furthermore, the teaching according to the invention also encompasses the structure of the wipes from two or more materials, in particular with regard to the absorption and permeability of the different wipe layers.

Suitable substrates are also for example either textile fibers made of natural fibers such as e.g. cellulose, silk, wool, regenerated cellulose (viscose, rayon), cellulose derivatives, or textile fibers made of synthetic fibers such as e.g. polyester, polypropylene, polyethylene terephthalate, polyamide, polyolefin, polyacrylonitrile fibers or mixtures of such fibers. These fibers can be woven or nonwoven.

EXAMPLES

All weight data in the examples are % by weight of active substance based on the total weight of the preparation

TABLE 1

Compositions according to the invention (concentrates)

| | Trade name (INCI) | 1 | 2 | 3 | 4 |
|---|---|---|---|---|---|
| (a) | Eumulgin ® HRE 40 (PEG-40 Hydrogenated Castor Oil)** | 30.0 | 28.5 | 28.5 | 5.0 |
| (b) | Cetiol ® HE (PEG-7 Cocoglycerides) | 61.5 | 65.5 | 63.5 | 87.0 |
| (d) | Monomuls ® 90-L 12 (Glyceryl Laurate) | | 3.0 | | |
| (d) | Monomuls ® 90-O 18 (Glyceryl Oleate) | 2.5 | | 3.0 | 3.0 |
| (c) | Propylene Glycol | 3.0 | | | |
| (c) | Glycerol | | 3.0 | 5.0 | 5.0 |
| (c) | Butylene Glycol | 3.0 | | | |
| | Appearance of the concentrate [RT] | clear | clear | clear | clear |
| | Viscosity of the concentrate [15° C.] | thin-liquid* | thin-liquid* | thin-liquid* | thin-liquid* |
| | Viscosity of the concentrate [RT] | thin-liquid* | thin-liquid* | thin-liquid* | thin-liquid* |
| | Stability of the concentrate [15° C., RT & 40° C.] after 1 week | stable | stable | stable | stable |
| | Stability of the concentrate [15° C., RT & 40° C.] after 8 weeks | stable | stable | stable | stable |
| | Dilutions with water & preservative [RT & 40° C.] | stable | stable | stable | stable |

**the proportion of ethoxylated triglycerides in the commercial product Eumulgin ® HRE 40 is ca. 85% by weight;
RT = room temperature 23° C.;
*thin-liquid: the viscosity is below 400 mPas (Brookfield RVF, 23° C., spindle 5, 10 rpm).

Aqueous Dilutions of the Compositions According to the Invention

Dilutions were prepared from the compositions 1 to 3 according to the invention (see table 1) by adding water and optionally further constituents. These are listed in the tables below:

TABLE 2

| Trade name (INCI) | 1 | 2 | 3 | 4 | 5 | 6 |
|---|---|---|---|---|---|---|
| Concentrate 1, 2 or 3 as per Tab. 1 | 1.0 | 2.0 | 4.0 | 1.5 | 3.0 | 1.5 |
| Uniphen ® P 23 | | | | 0.2 | | 0.2 |
| Nipaguard ® BPX | | 0.5 | | | | |
| Sodium Benzoate | 0.5 | | | 0.5 | | 0.5 |
| Euxyl PE ® 9010 | | | 1.0 | | | |
| Nipaguard ® PO 5 | | | | | 1.0 | |
| *Helianthus Annuus* Seed Oil | 0.1 | | | | | |
| Cetiol ® 868 (Ethylhexyl Stearate) | | | | 0.1 | | |
| Cetiol ® Sensoft (Propylheptyl Caprylate) | | | | | | 0.1 |
| Cetiol ® SN (Cetearyl Isononanoate) | | 0.1 | | | | |
| Propylene Glycol | | | | | 1.0 | 1.0 |
| Eumulgin ® HRE 40 (PEG-40 Hydrogenated Castor Oil) | | | | | | 0.8 |
| Perfume | 0.1 | | | 0.1 | | 0.1 |
| Water | | | ad 100 | | | |
| pH (optionally adjust with pH adjuster) | 4.5-5.5 | 6.0-6.5 | 6.0-6.5 | 4.5-5.5 | 5.0-6.5 | 4.5-5.5 |
| Stability of the dilution [RT] | stable | stable | stable | stable | stable | stable |

TABLE 3

| Trade name (INCI) | 7 | 8 | 9 | 10 | 11 |
|---|---|---|---|---|---|
| Concentrate 1, 2 or 3 as per Tab. 1 | 3.5 | 2.0 | 4.5 | 0.5 | 2.0 |
| Uniphen ® P 23 | | | 1.0 | | |
| Nipaguard ® BPX | | | | | 0.5 |
| Sodium Benzoate | | 0.5 | | 0.5 | |
| Sensiva SC 10 | 0.8 | | | | |
| Eumulgin ® HRE 40 (PEG-40 Hydrogenated Castor Oil) | | | 1.0 | | |
| Cosmedia ® SP (Sodium Polyacrylate) | | | | | 0.1 |
| Copherol ® 1250 C (Tocopheryl Acetate) | 0.1 | | | | 0.1 |
| Dihydroxyacetone (DHA) | | 2.0 | | | |
| Insect Repellent 3535 ® (Ethyl Butylacetyl-aminopropionate) | | | | 10.0 | |
| Herbalis ® G Ginkgo | | | | | 0.2 |
| Perfume | | | | | 0.1 |
| Water | | | | ad 100 | |
| pH (optionally adjust with pH adjuster) | 6.0-6.5 | 3.5-4.0 | 6.0-6.5 | 4.5-5.5 | 6.0-6.5 |
| Stability of the dilution [RT] | stable | stable | stable | stable | stable |

All dilutions (in each case with concentrate 1, 2 or 3) were stable at room temperature. The concentrates 1 to 3 and the dilutions prepared therefrom as per table 2 can be applied to the substrates.

Table 4 shows further dilutions of the compositions according to the invention

| Trade name (INCI) | 12 | 13 | 14 | 15 | 16 | 17 |
|---|---|---|---|---|---|---|
| Concentrate 3 as per Tab. 1 | 1.0 | 1.5 | 1.0 | 1.0 | 1.0 | 1.0 |
| Cetiol ® 868 (Ethylhexylstearate) | 0.1 | 0.1 | — | — | — | — |
| Eutanol ® G (Octyldodecanol) | — | — | — | — | — | 0.1 |
| Dehyton ® DC (Disodium Cocoamphodiacetate) | — | — | 0.5 | — | — | — |
| HYDAGEN ® C.A.T. (Triethyl Citrate) | — | — | 0.5 | — | — | — |
| ELESTAB ® HP 100 (Hexamidine diisethionate) | — | — | — | — | — | 0.1 |
| Panthenol | 0.5 | — | — | — | — | — |
| Hydagen ® B (Bisabolol) | — | 0.5 | — | — | — | — |
| Aloe Extract (Aloe Barbadensis) | — | — | — | — | 0.1 | — |
| Preservative | qs | qs | qs | — | qs | — |
| Perfume | — | qs | qs | — | qs | qs |
| Isopropanol | — | — | — | 5.0 | — | — |
| Cetylpyridonium Chloride | — | — | — | 0.1 | — | 0.1 |
| KOH (1%) | — | — | — | qs | — | qs |
| Water | 98.4 | 97.9 | 97.2 | 98.7 | 98.8 | 98.7 |
| Viscosity [mPas] (Brookfield RVF spindle 4, 10 rpm, 23° C.) | <100 | <100 | <100 | <100 | <100 | <100 |
| pH (optionally adjust with pH adjuster) | <5.5 | <5.5 | <5.5 | <5.5 | <5.5 | <5.5 |
| Stability of the dilution [RT] | stable | stable | stable | stable | stable | stable |

Dilutions 12, 13 and 14 are particularly suitable for treating substrates which are then used for cleansing the skin. Dilutions 15 and 17 are suitable in particular for treating substrates which are then used for disinfecting the skin. Dilution 16 is suitable in particular for treating substrates which are then used as intimate care products.

APPENDIX

Preservatives and Boosters Used: Trade Name and INCI Name

Uniphen® P 23 INCI: Phenoxyethanol, Methylparaben, Ethylparaben, Propylparaben, Butylparaben, Isobutyl-paraben; Nipaguard® BPX INCI: Phenoxyethanol, Methylparaben, Propylparaben, 2-bromo-2-Nitropropane-1,3-diol; Euxyl PE® 9010 INCI: Phenoxyethanol, Ethylhexylglycerin; Nipaguard® PO 5 INCI: Phenoxyethanol, Piroctone Olamine; Sensiva SC 10 INCI: Caprylyl Glycol, Ethylhexylglycerin.

Example S1

Substrate Treated with Composition According to the Invention

A three-layer nonwoven from Pelytex consists on the outside of 22 grams per square meter of polypropylene and on the inside of viscose/polypropylene (75/25; 80 grams per square meter). A section measuring 18×14 cm is sprayed on one side with 1.5 g of the concentrate as per example 1 (table 1).

Example S2

Substrate Treated with Composition According to the Invention

A spunlace substrate from Jacob Holm consisting of 40% viscose and 60% PET, 50 grams per square meter measuring 180×200 mm was treated with 5 g of a composition as per example 5 in table 2.

Comparative Examples

As comparative example, example 2 from DE 10 2005 006 299 A1 was reworked. In contrast to the concentrates according to the invention, the prior art product is thick-liquid at 15° C. and therefore difficult to pump. Furthermore, storage at 40° C. for one day results in separation.

TABLE 5

| | Trade name (INCI) | Comparative example |
|---|---|---|
| | Dehymuls ® HRE 7 (PEG-7 Hydrogenated Castor Oil) | 54 |
| | Eumulgin ® B1 (Cetheareth-12) | 13.5 |
| (a) | Eumulgin ® HRE 40 (PEG-40 Hydrogenated Castor Oil)** | |
| (b) | Cetiol ® HE (PEG-7 Cocoglycerides) | |
| (d) | Monomuls ® 90-O 18 (Glyceryl Oleate) | 7.5 |
| (c) | Glycerin | 5.0 |
| | Water | 20 |
| | Viscosity of the concentrate [15° C.] | Thick-liquid*** |
| | Stability of the concentrate at 40° C. after 1 day | Separation |

***thick-liquid: the viscosity is more than 100 000 mPas (Brookfield RVF, 23° C., spindle TE, 4 rpm)

The dilutions obtained from the comparative example were also not stable; the results are shown in table 6.

TABLE 6

| Trade name (INCI) | C1 | C2 | C3 |
|---|---|---|---|
| Concentrate as per comparative example (table 5) | 1.0 | 2.0 | 4.0 |
| Uniphen ® P 23 | | | |
| Nipaguard ® BPX | | 0.5 | |
| Sodium Benzoate | 0.5 | | |
| Euxyl PE ® 9010 | | | 1.0 |
| Nipaguard ® PO 5 | | | |
| *Helianthus Annuus* Seed Oil | 0.1 | | |
| Cetiol ® 868 (Ethylhexyl Stearate) | | | |
| Cetiol ® Sensoft (Propylheptyl Caprylate) | | | |
| Cetiol ® SN (Cetearyl Isononanoate) | | | 0.1 |
| Propylene Glycol | | | |
| Eumulgin ® HRE 40 (PEG-40 Hydrogenated Castor Oil) | | | |
| Perfume | 0.1 | | |
| Water | | ad 100 | |
| pH (optionally adjust with pH adjuster) | 4.5-5.5 | 6.0-6.5 | 6.0-6.5 |
| Stability of the dilution [after storage for 1 day at RT] | unstable | unstable | unstable |

What is claimed is:

1. A composition consisting essentially of:
a. at least one compound selected from the group consisting of
  i. hydrogenated and/or nonhydrogenated, ethoxylated and/or propoxylated triglycerides of ricinoleic acid with a degree of ethoxylation and/or degree of propoxylation of greater than or equal to 20,
  ii. addition products of from 2 to 50 mol of ethylene oxide onto sorbitan mono- and/or diesters of saturated or unsaturated fatty acids having 6 to 22 carbon atoms, and
  iii. addition products of from 2 to 50 mol of ethylene oxide and 1 to 20 mol of propylene oxide onto alpha-olefin epoxides having 8 to 22 carbon atoms and ring-opened with polyols;
b. at least one ethoxylated and/or propoxylated glycerol fatty acid mono- and/or diester with a degree of ethoxylation of less than 20;
c. at least one polyol selected from the group consisting of glycerol, diglycerol, triglycerol, tetraglycerol, alkylene glycols and polyalkylene glycols;
d. at least one glycerol fatty acid monoester of the general formula (I)

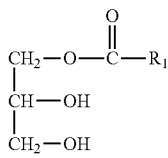

wherein $R_1$ is a saturated or unsaturated, branched or linear radical having 9 to 19 carbon atoms; and
e. less than or equal to 20% by weight of water;
wherein the composition comprises no ethoxylated emulsifiers having an HLB value less than or equal to 6.

2. The composition of claim 1, consisting essentially of, based on the total weight of the composition,
3 to 50% by weight of at least one component (a);
40 to 90% by weight of at least one component (b);
1 to 10% by weight of at least one component (c);
0.5 to 5% by weight of at least one component (d); and
less than or equal to 20% by weight of water.

3. A method for treating substrates, the method comprising applying a composition to a substrate, followed by optionally drying the substrate, wherein the composition consists essentially of the following constituents:
a. at least one compound selected from the group consisting of
  i. hydrogenated and/or nonhydrogenated, ethoxylated and/or propoxylated triglycerides of ricinoleic acid with a degree of ethoxylation and/or degree of propoxylation of greater than or equal to 20,
  ii. addition products of from 2 to 50 mol of ethylene oxide onto sorbitan mono- and/or diesters of saturated or unsaturated fatty acids having 6 to 22 carbon atoms, and
  iii. addition products of from 2 to 50 mol of ethylene oxide and 1 to 20 mol of propylene oxide onto alpha-olefin epoxides having 8 to 22 carbon atoms and ring-opened with polyols,
b. at least one ethoxylated and/or propoxylated glycerol fatty acid mono- and/or diester with a degree of ethoxylation of less than 20,
c. at least one polyol selected from the group consisting of glycerol, diglycerol, triglycerol, tetraglycerol, alkylene glycols and polyalkylene glycols,
d. at least one glycerol fatty acid monoester of the general formula (I)

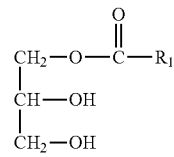

wherein $R_1$ is a saturated or unsaturated, branched or linear radical having 9 to 19 carbon atoms
e. less than or equal to 20% by weight of water;
wherein the composition comprises no ethoxylated emulsifiers having an HLB value less than or equal to 6.

4. The composition of claim 1, wherein the hydrogenated and/or nonhydrogenated, ethoxylated and/or propoxylated triglycerides of ricinoleic acid have a degree of ethoxylation and/or degree of propoxylation of from 20 to 60.

5. The composition of claim 1, wherein the at least one ethoxylated and/or propoxylated glycerol fatty acid mono- and/or diester has a degree of ethoxylation of from 3 to 19.

6. The composition of claim 5, wherein the at least one ethoxylated and/or propoxylated glycerol fatty acid mono- and/or diester has a degree of ethoxylation of from 3 to 15.

7. The composition of claim 2, consisting essentially of, based on the total weight of the composition:
5 to 45% by weight of at least one component (a);
50 to 85% by weight of at least one component (b);
2 to 8% by weight of at least one component (c);
1 to 3% by weight of at least one component (d); and
less than or equal to 20% by weight of water.

8. The composition of claim 7, consisting essentially of, based on the total weight of the composition:
10 to 40% by weight of at least one component (a);
55 to 80% by weight of at least one component (b);
3 to 6% by weight of at least one component (c);
1 to 3% by weight of at least one component (d); and
less than or equal to 20% by weight of water.

9. The method of claim 3, wherein the hydrogenated and/or nonhydrogenated, ethoxylated and/or propoxylated triglycerides of ricinoleic acid have a degree of ethoxylation and/or degree of propoxylation of from 20 to 60.

10. The method of claim 3, wherein the at least one ethoxylated and/or propoxylated glycerol fatty acid mono- and/or diester has a degree of ethoxylation of from 3 to 19.

11. The method of claim 10, the at least one ethoxylated and/or propoxylated glycerol fatty acid mono- and/or diester has a degree of ethoxylation of from 3 to 15.

12. The composition of claim 1, wherein the weight ratio of component (b) to component (a) is greater than or equal to 1.

13. The composition of claim 1, further comprising one or more of a perfume, a further oil, a preservative, an UV light protection factor, a biogenic active ingredient, dihydroxyacetone, an insect repellent, an anti-inflammatory active ingredient, or a disinfectant.

* * * * *